United States Patent

Ekwall

[11] Patent Number: 5,824,016
[45] Date of Patent: Oct. 20, 1998

[54] MEDICAL DEVICE USED TO STIMULATE TISSUE

[75] Inventor: Christer Ekwall, Spånga, Sweden

[73] Assignee: Pacesetter AB, Solna, Sweden

[21] Appl. No.: 791,114

[22] Filed: Jan. 30, 1997

[30] Foreign Application Priority Data

Feb. 2, 1996 [SE] Sweden .................................. 9600389

[51] Int. Cl.$^6$ ................................................. A61N 1/375
[52] U.S. Cl. ............................................... 607/9; 607/121
[58] Field of Search .................................... 607/9, 121

[56] References Cited

U.S. PATENT DOCUMENTS

| 4,336,811 | 6/1982 | Beck et al. . | |
| 5,282,844 | 2/1994 | Stokes et al. | 607/121 |
| 5,571,158 | 11/1996 | Bozz et al. | 607/121 |

FOREIGN PATENT DOCUMENTS

| 0 032 356 | 7/1981 | European Pat. Off. . | |
| 0 453 117 | 10/1991 | European Pat. Off. . | |
| 0 475 027 | 3/1992 | European Pat. Off. . | |
| 2056493 | 5/1972 | Germany | 607/121 |

OTHER PUBLICATIONS

"Electromechanical Methods, Fundamentals and Applications," Bard et al., ISBN 0–471–05542–5, pp. 8–10.
"New Perspectives in Cardiac Pacing," Barold et al., (1988), p. 4.

*Primary Examiner*—William E. Kamm
*Attorney, Agent, or Firm*—Hill & Simpson

[57] ABSTRACT

An implantable medical device has a pulse generator for generating electrical pulses, an electrical energy storage element connectable to an output stage, and an electrode arrangement for conducting the electrical pulses to tissue, the electrode arrangement having an input end and an output end. The output means of the pulse generator is connectable to the input end of the electrode arrangement, and the capacitance of the output stage is less than 1 $\mu$F and the electrode arrangement has a capacitor with a capacitance greater than 1 $\mu$F.

14 Claims, 2 Drawing Sheets

5,824,016

MEDICAL DEVICE USED TO STIMULATE TISSUE

BACKGROUND OF THE INVENTION

1. Field of the Invention

The present invention relates to implantable medical devices used to stimulate tissue.

2. Description of the Prior Art

Electrodes are used in implantable medical devices to stimulate tissue or to transmit signals from tissue to a sensing device. In implantable pacemakers, for example, stimulating electrodes form part of a stimulation circuit which includes a stimulation pulse generator connected to a coupling capacitor which is connected to a stimulation electrode fixed in or near the heart. The return path of the circuit to the pacemaker is usually through the intervening body tissues to an indifferent electrode on the casing of the pacemaker.

A stimulation pulse generator in an implanted pacemaker contains pulse generator capacitors which are charged by the pacemaker battery to a desired stimulation voltage and are discharged through the stimulation electrode when the pacemaker controller calls for a stimulation pulse to be emitted. As soon as the pulse has been discharged the pulse generator capacitors are recharged to their predischarge voltage levels.

A type of stimulation electrode known from U.S. Pat. No. 4,336,811 has a metal tip covered by a non-metallic coating of a compound of the metal in the tip, and a two-layer membrane. In one embodiment of the electrode the metal is silver and the compound is silver chloride. In order to prevent the movement of soluble ions of the tip coating from migrating into body tissues during use, the tip is covered by a two-layer membrane. The inner membrane layer inhibits movement into the body tissue of soluble ions of the coating on the electrode, which may be toxic to the surrounding body tissue. The outer membrane layer is composed of material which is non-toxic to body tissue.

Leakage currents arise in the stimulation circuit from electrons migrating by "tunneling" through the semiconductor materials used as switches in the pacemaker circuitry. Measurements taken at the terminals of pacemakers give leakage current values of the order of 1 nano-Ampere ($1 \times 10^{-9}$ A). It is important that there is no, or as little as possible, leakage current from the electrodes to the surrounding tissue. This is because leakage currents can cause the growth of fibrous tissue around the electrodes which lead to increased stimulation thresholds, high current consumption and hence reduced battery life. A further problem with leakage currents is that under their influence some electrode materials will electrolyze when in contact with body fluids, which leads to damaged electrodes and contaminated body tissues.

In order to prevent leakage currents from the charged stimulation pulse capacitors an extra capacitor, known as a coupling capacitor, with a capacitance usually in the range of 1–15 $\mu$F, is positioned in the circuit between the stimulation pulse capacitors and the electrode. Such a coupling capacitor effectively isolates the lead connector from the electronic switches is described, for example, in European Application 323 56. The use of a coupling capacitor has disadvantages, for example, a coupling capacitor is an additional component which adds to the cost of the pacemaker and makes it more complicated to construct.

A further disadvantage of using coupling capacitors arises when they are used in Autocapture pacemakers. In Autocapture pacemakers it is essential that the evoked response to a stimulation impulse can be sensed. Using a single stimulation impulse leads to polarization, i.e., ionization, of the fluid between the electrode tip and the surrounding tissue, which leaves it with an electrical potential. This electrical potential, known as the polarization voltage, is zero prior to the emission of a stimulation pulse, rises exponentially during the pulse and falls inversely exponentially after the end of the pulse. To avoid the problem of the polarization voltage of the tissue around the electrode tip masking the evoked response signal, it is usual to use a biphasic stimulation complex in which a pulse of specified energy is quickly followed by a second pulse of equal energy but with the opposite polarity. The net sum of the polarization voltage is zero and hence polarization is eliminated. The use of a coupling capacitor complicates the design and production of pacemakers using biphasic stimulation pulses and also causes an increase in the time required to perform the polarization cancellation procedure.

SUMMARY OF THE INVENTION

An object of the present invention is to prevent leakage currents in the output circuit of a medical device for stimulating tissue.

In accordance with the invention, this object is accomplished in a medical device by utilization of the electrode lead-to-tissue electrolytic interface capacitance (Helmholtz capacitance) with a highly leakage resistant layer interface together with formed, e.g., by titanium or titanium dioxide. Under certain conditions, e.g., by the addition of a small bias current, this layer can even be made "self healing." This makes the use of a coupling capacitor in the output part of the medical device unnecessary which leads to a medical device of simplified design and construction and which used the energy stored therein in a more efficient manner.

DESCRIPTION OF THE PREFERRED EMBODIMENTS

Figure 1:
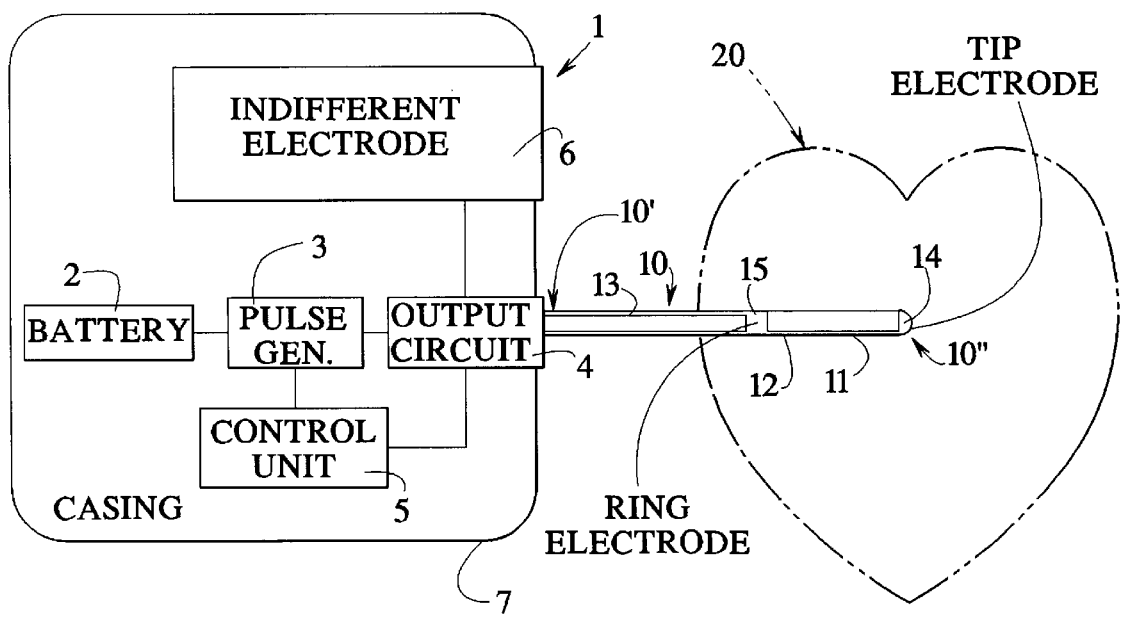
FIG. 1 is a block diagram of an embodiment of a pacemaker and electrode constructed in accordance with the principles of the present invention.
Figure 2:
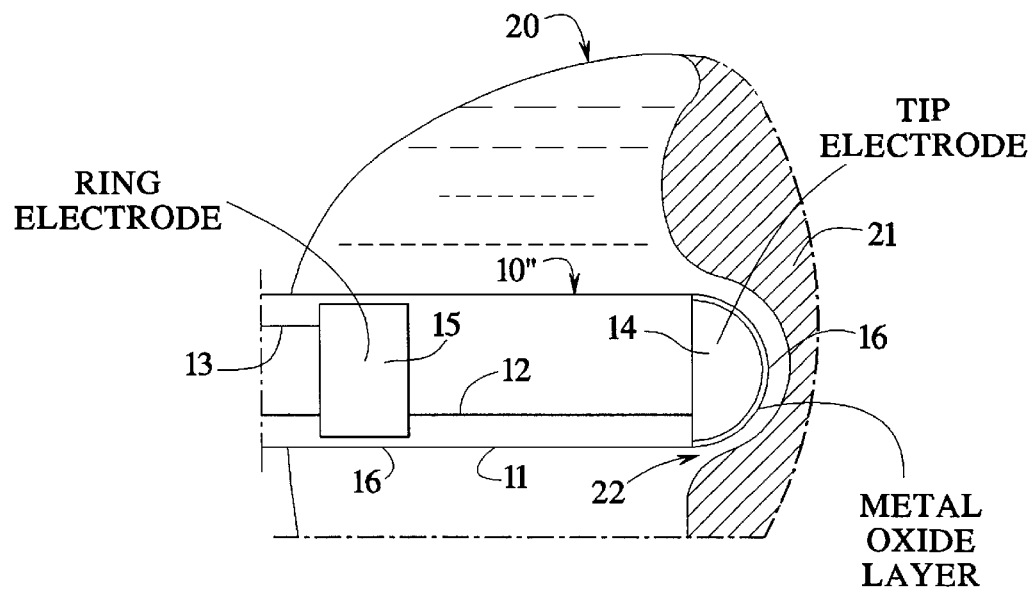
FIG. 2 shows a cross-section through the electrode shown in FIG. 1 constructed in accordance with the principles of the present invention.

FIG. 1 shows one embodiment of the invention wherein the medical devices is an Autocapture pacemaker. FIG. 1 represents an Autocapture pacemaker 1 having a battery 2, a pulse generator 3 connected to an output circuit 4, a control unit 5 and indifferent electrode 6 mounted on the casing 7. An electrode arrangement 10 has an input end 10' connectable to the output circuit 4, and an output end 10" implantable in body tissue. Output circuit 4 provides a connection between the pulse generator 3 and the electrode arrangement 10 and has a negligible capacitance, less than 1 $\mu$F, and a negligible resistance. In the embodiment of FIG. 1, the electrode arrangement 10 is an electrode lead 11 containing insulated metal conductors 12 and 13 leading to the output end 10" with a tip electrode 14 and a ring electrode 15, for connecting the output circuit 4 to a heart 20 and for conducting stimulation pulses to the heart 20 via heart tissue 21 and heart fluids 22.

The control unit 5 has known means for determining when a stimulation pulse is required and for determining the impedance of the pulse circuit so that the correct stimulation energy reaches the heart. These means will not be described further as they do not form part of the present invention. Stimulation pulse energy is stored in a reservoir capacitor 8 in the pulse generator 3 and the capacitor 8 is connected by semiconductor switching stage 9 via the output circuit 4 to the conductors 12 and 13. After a stimulation pulse is discharged, the capacitor 8 is charged to a predetermined voltage using the energy stored in the battery 2.

The tip electrode 14 and the ring electrode 15 in this embodiment are made of titanium covered with a contact surface made of a thin layer of non-metallic titanium oxide 16. Titanium oxide is a very good electrical insulator, that is, it has a high dielectric constant, and is hard, stable and a very good biocompatible material. Furthermore a titanium oxide layer grown in a titanium-to-liquid interface does not degrade for moderate reversed voltages. The titanium oxide layer 16 can be provided on the electrodes before implantation or can be grown on the electrodes after implantation, for example, as follows. The electrode titanium surfaces can easily react with hydroxy ions in a liquid such as the heart fluids 22 surrounding the implanted electrodes 14 and 15 to form a layer of titanium oxide 16 on the surface of the metal. This process is enhanced by passing an electrical current at a voltage which is less than the stimulation pulse voltage across the liquid-to-metal interface, with titanium as the anode.

The insulating effect of the titanium oxide can be used to automatically limit the thickness of the titanium oxide layer 16 when it is being formed by a current flow. As the thickness and hence the resistance of the titanium oxide layer increases, the current will decrease and eventually stop when the titanium oxide layer is so thick that its resistance is sufficiently high to prevent current flow at the low voltage across it. The resulting titanium oxide layer thickness is proportional to the voltage that was used to produce it. A voltage of 9 V, for example, gives a layer on the order of 1 $\mu$m thick. For low to moderate voltages the titanium oxide layer will be very thin, possibly only one molecule thick. Such thin layers of dielectric materials have a high capacitance and by choosing an appropriate voltage it is possible to control the capacitance of the resulting capacitor. By forming a capacitor with a capacitance between 1–15 $\mu$F it is possible to use this layer as a coupling capacitor and thereby avoid the need to design and produce a coupling capacitor in the pulse generator 3.

A lower voltage than that used to form a titanium oxide layer when applied across an intact titanium oxide layer 16 will not result in any current flow. If, however, the titanium oxide layer 16 is damaged or scratched at any point then a current will start to flow at this point if the resistance at this point is low enough to allow a current to flow. If the current is caused by a voltage source with the titanium as the anode then the current will cause titanium oxide to form (or become thicker) at this low resistance point thereby causing the insulating layer to self-heal. The current flow will stop when the titanium oxide layer 16 is thick enough. By ensuring that the titanium is always the anode with respect to the surrounding fluid it is possible to repair damage to the titanium oxide layer 16.

Since the stimulation pulses represent an alternating voltage (or AC current), the stimulation pulses are still able to pass through the titanium oxide layer 16 and stimulate the heart 20.

In a second embodiment, aluminum is used for the electrodes 14 and 15 instead of titanium and an aluminum oxide layer is grown on the surface of the electrode. Of course any other suitable substance which, when subjected to an electrical current, can form an insulating surface layer can be used instead of aluminum and titanium.

The stimulation charge is stored in capacitor 8. The switches 9' and 9" are normally positioned in the center position. By closing switch 26 the capacitor 8 is charged via resistor 25 from the battery. As the voltage at the simulation capacitor 8 reaches the Vref level the comparator 26 opens the switch inhibiting further charging. The stimulation level Vref is selected from the controller 5 via an digital-to-analog converter 23 allowing any value or algorithmic change of value within the limits of the digital-to-analog converter. It should be noted that by a modification of the circuit by disconnection of lead 10 to terminal 10' and connection of terminal 10' to ground a single lead stimulation between the lead tip and the pacemaker casing is possible (unipolar stimulation). At the moment of stimulation, decided by the controller, the switches 9' and 9" are, for the duration of the stimulus, changed to their end position in such a way that switch 9' is in its upper position switch 9" is in the lower position. This will result in a positive stimulation impulse via terminal 12 to the lead tip connector 22. Similarly with switch 9' in the lower position and switch 9" in its upper position, a negative stimulation impulse result at the lead tip 22.

Figure 3:
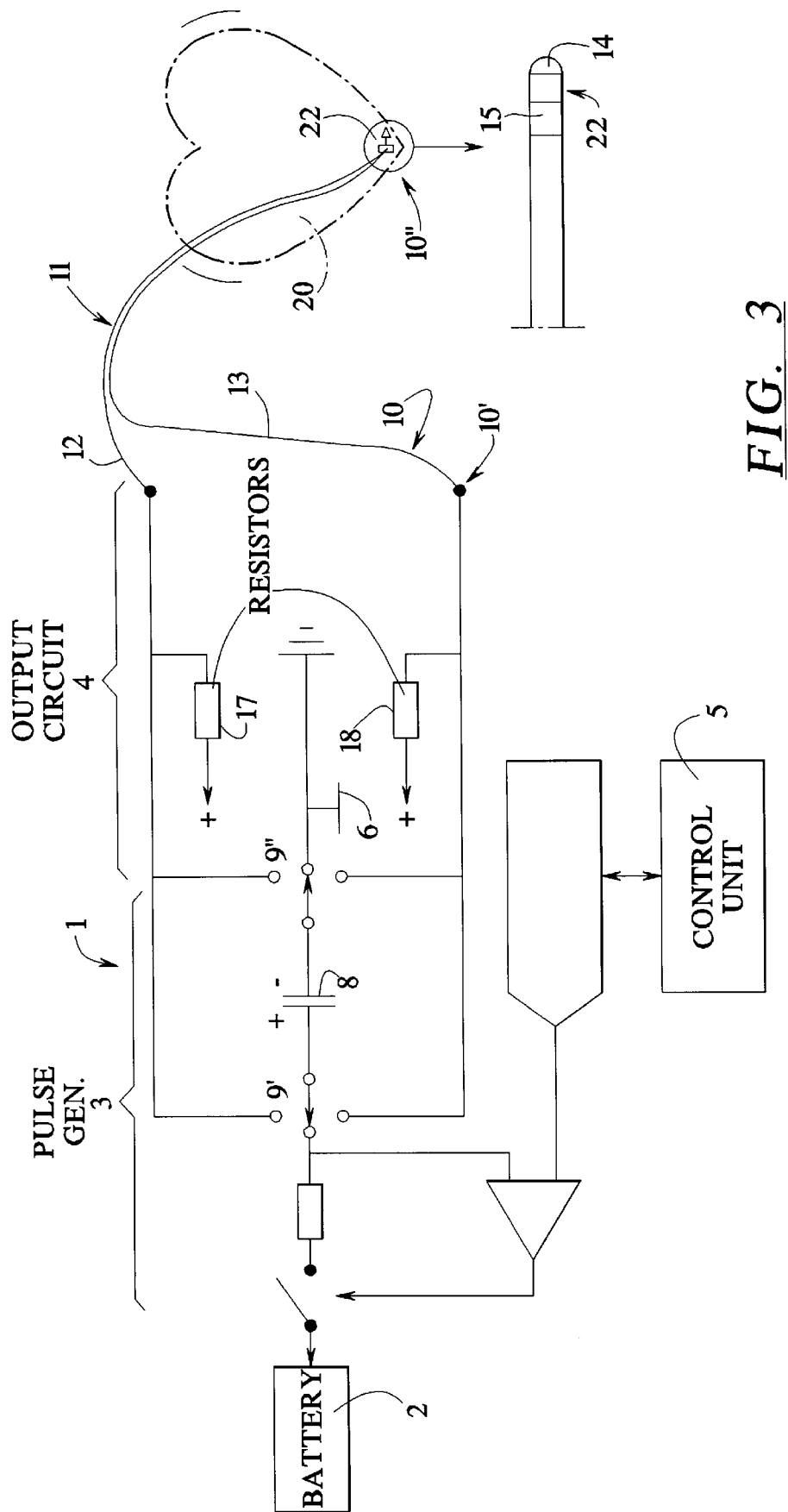
FIG. 3 is a circuit diagram of another embodiment of the invention.

In a third embodiment of the invention, as shown in the circuit diagram in FIG. 3, resistors 17 and 18 each have a resistance which is high compared to the of resistance of the electrical path between the output of the pacemaker to the indifferent electrode 6 via the electrodes 14 and 15, the titanium oxide layer 16, the heart 20 and body tissues. The resistors 17 and 18 are connected in the output stage 4 between each electrode 12 and 13 and the positive supply. For pacemakers using pulse generators which generate 3 volt pulses, resistors with a resistance of 10 M'Ω would give a current of 30 nano-Ampere ($30 \times 10^{-9}$ A). These resistors 17 and 18 bias the semiconductor switches 9' and 9" such that in the event of a leakage current which is normally of the order of only 1 nano-Ampere ($1 \times 10^{-9}$ A) i.e., only one thirtieth of the bias current, the titanium electrodes 12 and 13 are always positive with respect to the liquid 22 surrounding them. In this way leakage currents produce a bias current which operates to cause an increase in the thickness of the titanium oxide layer, which leads to increased resistance and eventually the elimination of the leakage current.

In a fourth embodiment the control unit 5 measures the impedance of the stimulation circuit in order to determine if the oxide layer has been damaged, thereby reducing the thickness of the oxide layer and hence increasing the leakage currents. If the leakage of the oxide layer is too high, then control means 5 allows a low voltage bias current to flow across the electrode. This causes the damaged oxide layer to regrow and restores the capacitance of the layer. When the leakage current has reached a sufficiently low value, then the low voltage bias current is stopped.

In a fifth embodiment of the present invention the oxide layer is protected by a protective membrane of semipermeable material, for example naphion, termeon or carboxylic acid resin.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable medical device for stimulating tissue comprising:

a housing adapted for implantation in a subject;

a pulse generator in said housing which emits electrical pulses, said pulse generator containing means for storing electrical energy and for discharging said electrical energy to form said electrical pulses;

electrode means adapted for implantation in said subject for conducting said electrical pulse in vivo to tissue, said electrode means having an input end, and an output end from which said electrical pulses are delivered;

an output stage disposed in said housing connected between said pulse generator and said input end of said electrode means; and said output stage having a capacitance which is less than 1 $\mu$F and said electrode means having a capacitive element with a capacitance greater than 1 $\mu$F.

2. An implantable medical device as claimed in claim 1 wherein said electrode arrangement comprises at least one electrical conductor made of a metal, and an electrode, said electrode being connected to said at least one conductor and being disposed at said output end of said electrode means, and wherein said capacitive element comprises a layer of an electrically insulating compound of said metal formed on said electrode.

3. An implantable medical device as claimed in claim 2 wherein said metal comprises titanium.

4. An implantable medical device as claimed in claim 2 wherein said metal comprises aluminum.

5. An implantable medical device as claimed in claim 2 wherein said compound comprises an oxide of said metal.

6. An implantable medical device as claimed in claim 1 further comprising a plurality of high resistance biasing resistors contained in said housing and connected for making any leakage current from said pulse generator to said electrode means electrically positive with respect to said tissue.

7. An implantable medical device as claimed in claim 2 further comprising a semi-permeable membrane covering said layer on said electrode.

8. An implantable medical device as claimed in claim 1 further comprising control means for operating said pulse generator for emitting said electrical pulses at an amplitude level and at a rate for pacing a heart, and wherein said tissue comprises cardiac tissue.

9. An implantable medical electrode cable for delivering electrical pulses in vivo to body tissue, said electrode cable comprising an input end into which said pulses are supplied and an output end from which said pulses are delivered to said tissue, with at least one electrical conductor extending between said input end and said output end, and said electrode cable having a capacitive element with a capacitance of more than 1 $\mu$F.

10. An electrode cable as claimed in claim 9 wherein said at least one conductor is made of metal, and said cable having an electrode at said output end, and wherein said capacitive element comprises a layer of an electrically insulating compound of said metal formed on said electrode.

11. An electrode cable as claimed in claim 10 wherein said metal comprises titanium.

12. An electrode cable as claimed in claim 10 wherein said metal comprises aluminum.

13. An electrode cable as claimed in claim 10 wherein said compound comprises an oxide of said metal.

14. An electrode cable as claimed in claim 10 further comprising a semipermeable membrane covering said layer.

* * * * *